United States Patent [19]

Chong

[11] Patent Number: 5,077,102
[45] Date of Patent: Dec. 31, 1991

[54] SCENTED ARTIFICIAL FLOWER

[76] Inventor: Sue C. Chong, 2758 Orange Ave. #1, Torrance, Calif. 90501

[21] Appl. No.: 669,605

[22] Filed: Mar. 14, 1991

[51] Int. Cl.$^5$ ............................................. A41G 1/00
[52] U.S. Cl. ..................................... 428/24; 239/44; 428/905
[58] Field of Search ............... 428/24, 26, 25, 905; 239/44

[56] References Cited

U.S. PATENT DOCUMENTS

| | | | |
|---|---|---|---|
| 1,647,533 | 11/1927 | Matlack | 428/24 X |
| 2,471,949 | 5/1949 | Gilowitz | 428/24 X |
| 2,507,899 | 5/1950 | Gilowitz | 239/44 |
| 2,807,901 | 10/1957 | Gilowitz | 428/905 X |
| 3,400,890 | 9/1968 | Gould | 428/26 X |
| 3,679,133 | 7/1972 | Sekiguchi et al. | 239/145 X |
| 3,861,991 | 1/1975 | Kim | 428/26 X |
| 4,156,324 | 5/1979 | Henttonen | 405/43 X |
| 4,708,900 | 11/1987 | Siegers et al. | 428/24 X |
| 4,919,981 | 4/1990 | Levey et al. | 428/26 |
| 4,958,768 | 9/1990 | Ishihara | 239/34 |

FOREIGN PATENT DOCUMENTS 2408796 6/1979 France .

*Primary Examiner*—Henry F. Epstein
*Attorney, Agent, or Firm*—Richard C. Litman

[57] ABSTRACT

A scented artificial flower including a flower cup formed of petals, at least one stamen having a filament portion supporting an anther portion, said stamen being integral with an ovary portion, said integral stamen and ovary portion being formed of wick material, a supporting stem which may include a wick, and a perfume container connected to the supporting stem, whereby scented liquid in said perfume container may be moved to the anther portion, filament portion and ovary portion by capillary action, by pressure and by gravity either separately or by combining two or more forces, the scent being disbursed to the atmosphere through said integral stamen and ovary portion. By forming the petals of an absorbent material, the scented liquid is also transmitted from the ovary to the juxtaposed petals to further enhance the dispersion of the scented fluid.

8 Claims, 1 Drawing Sheet

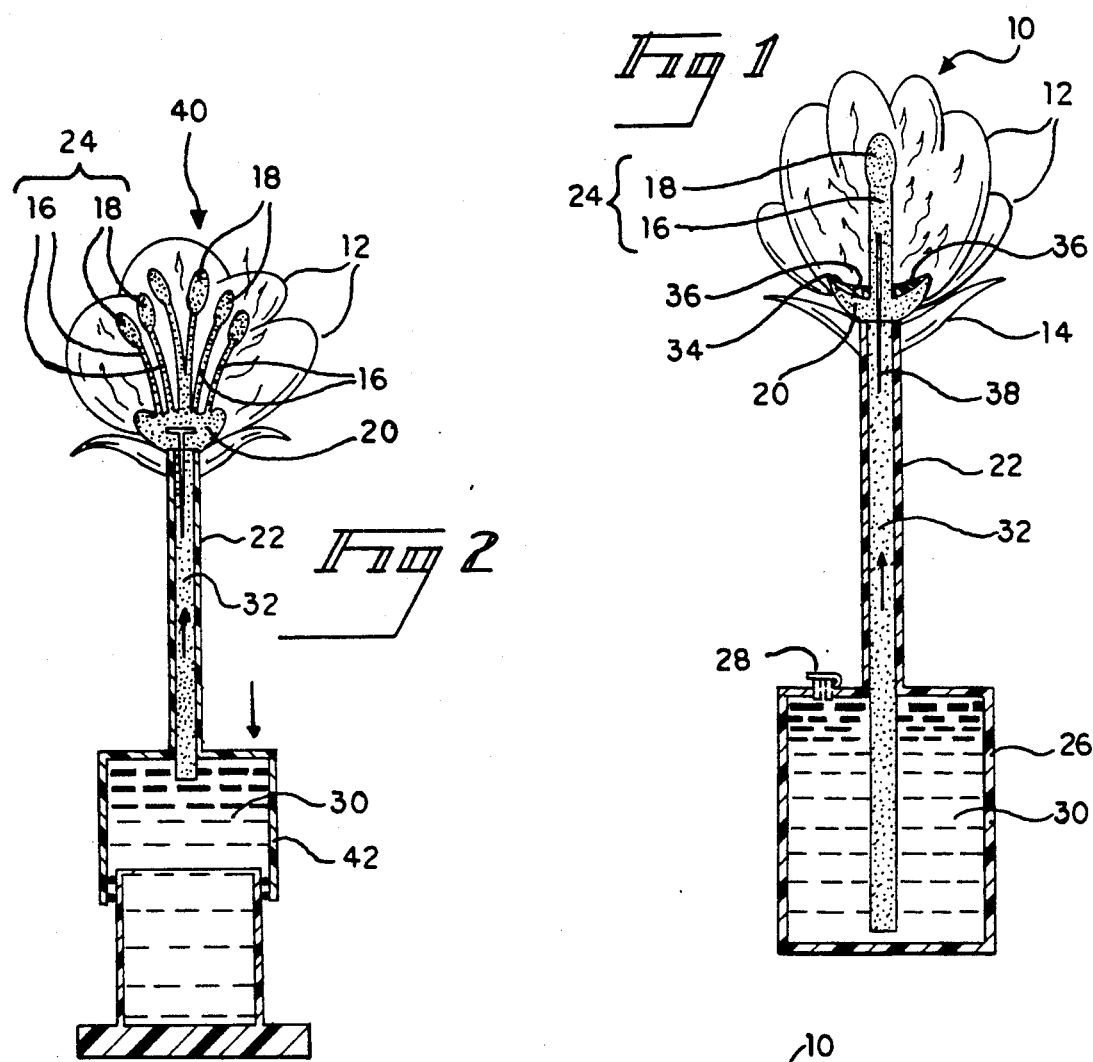
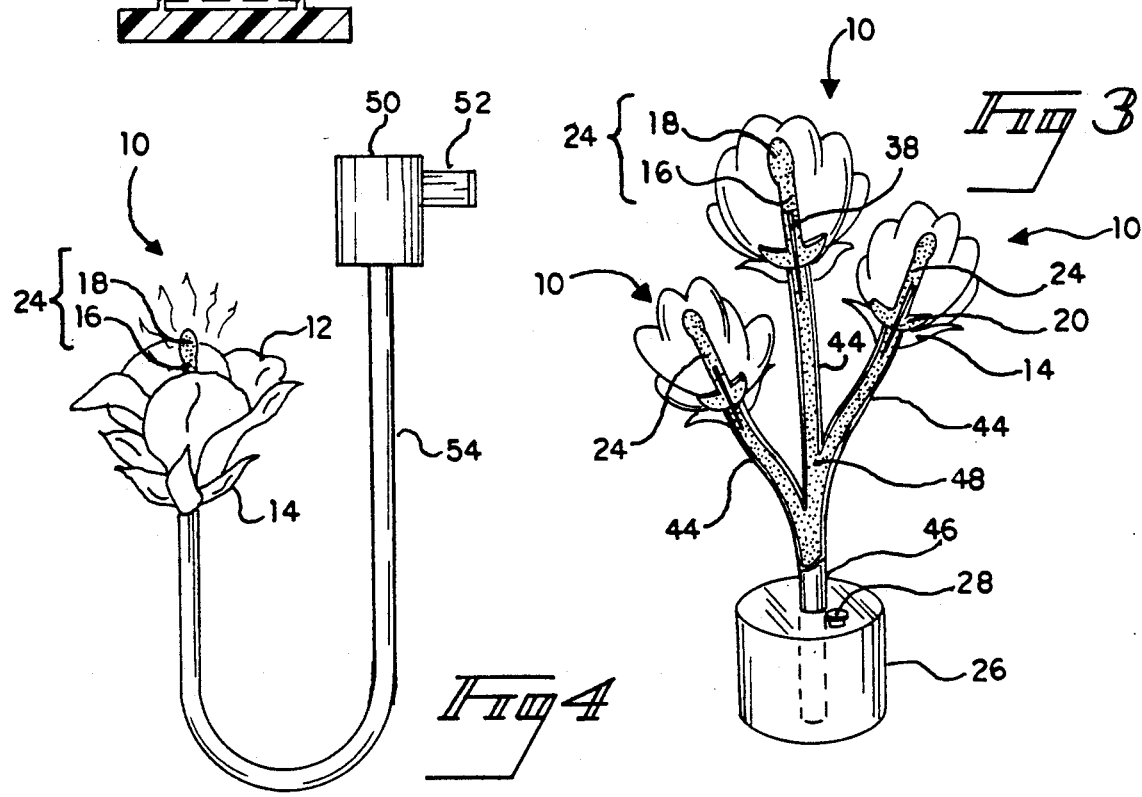

SCENTED ARTIFICIAL FLOWER

BACKGROUND OF THE INVENTION

1. Field of the Invention

This invention relates to a means for providing floral scents for artificial plants and flowers while retaining a natural appearance.

2. Description of Related Prior Art

Scented artificial flowers are well known in the prior art, the distribution of the scent being achieved in a variety of ways. U.S. Pat. No. 3,861,991 issued Jan. 21, 1975 to Won Cheol Kim discloses an arrangement wherein the sepal portion of the flower defines an inner reservoir for support of a truncated container of perfume. The perfume is distributed through the stamen components fed by a pistil member by capillary distribution. U.S. Pat. No. 4,708,900 issued Nov. 24, 1987 to Hans-Peter Siegers and Wilfried Macke discloses a fibrous perfume carrier for artificial flowers which is mounted on a wire which enters a hole in the carrier, the carrier and wire being located within the flower cup. The perfume carrier may be given a contour similar to a natural flower stamen. U.S. Pat. No. 4,919,981 issued Apr. 24, 1990 to John Levey and Idelle B. Levey discloses an air freshener in the form of an artificial flower in which the scent is distributed from a fluid container through wick-like stems into a simulated leaf pad and a sponge-like core. U.S. Pat. No. 4,958,768 issued Sept. 25, 1990 to Yoshiko Ishihara discloses an artificial potted flower wherein deodorant and/or perfume is entrapped in swollen gels of water-absorbent synthetic resin and released by the moisture-releasing property of water-absorbent resin in the case of a deodorant, or by inherent sublimability in the case of a perfume. French Patent No. 2,408,796 issued June 8, 1979 to Allen Lennard Pack and Philip Pack discloses an arrangement wherein the petals are attached to a wick immersed in a perfume, whereby the aroma is distributed by means of the petals. U.S. Pat. No. 3,679,133 issued July 25, 1972 to Masaaki Sekiguchi, Kaoru Yoshikawa, and Akira Komatsu disclose an apparatus for distributing perfume from a pressurized container. U.S. Pat. No. 4,156,324 issued May 29, 1979 to Anita T. Henttonen discloses a method and apparatus for artificial irrigation of flower beds and garden plots.

SUMMARY AND OBJECTS OF THE INVENTION

None of the foregoing patents disclose an arrangement wherein the perfume is distributed by means of a wick contained within an artificial stem, the wick terminating in the configuration of an anther within the flower cup, the perfume being distributed by the anther, which in a real flower is the part of the stamen which develops and contains the pollen, and which is usually borne on a stalk. In contact with the anther are flower petals which also may have the capability of producing a wicking action to further dissipate the perfume into the ambient atmosphere.

It is an object of this invention to provide a new and novel arrangement for providing floral scents for artificial plants and flowers while maintaining a natural appearance.

It is a further object of this invention to provide a new and novel arrangement for providing floral scents for artificial plants and flowers wherein the perfume is delivered by capillary action through a wick to the anther portion of the stamen.

It is still another object of this invention to provide an arrangement wherein perfume is delivered to the anther portion of the stamen of a flower under pressure.

It is a yet further object of this invention to provide an arrangement wherein perfume is delivered to the anther portion of a stamen of a flower by means of gravity.

An additional object of the invention is to provide an artificial flower arrangement wherein scented fluid is delivered to either or both the petals and anther portion of a flower stamen, from a remote fluid source, by capillary action, gravity feed or pressure action.

Other objects, features and advantages of this invention will be apparent from the following detailed description and the appended claims, reference being had to the accompanying drawing forming a part of the specification, wherein like reference numerals designate corresponding parts of the several views.

BRIEF DESCRIPTION OF THE DRAWINGS

FIG. 1 shows an artificial flower connected to a perfume supply by means of a wick to distribute a floral scent to the anther portion of a stamen and optionally, the petals of a flower cup.

FIG. 2 is a view similar to FIG. 1 schematically illustrating a pressurized container for the perfume supply.

FIG. 3 is a view similar to FIG. 1 showing a plurality of artificial flowers connected to a wick containing stems branching from a central stem connected to a perfume supply.

FIG. 4 shows an embodiment wherein the perfume disbursement is aided by gravity.

DETAILED DESCRIPTION OF THE PREFERRED EMBODIMENT

Before explaining in detail the present invention, it is to be understood that the invention is not limited in its application to the details of construction and arrangement of parts illustrated in the accompanying drawings, since the invention is capable of other embodiments and of being practiced or carried out in various ways. Also, it is to be understood that the phraseology and terminology employed herein is for the purpose of description and not limitation.

Turning now to FIG. 1, there is shown an artificial flower 10 having a number of component parts including petals 12 forming a flower cup, sepal 14, filament 16, anther 18, ovary 20 and stem 22. Filament 16 and anther 18 together form a stamen 24. Stem 22 is connected to a perfume supply container 26 which can be refilled through breather cap 28 with a scented liquid or perfume 30 designed to have the natural scent of the flower which is artificially duplicated. Contained within the stem is a wick 32 which connects container 26 to the stamen 24. Perfume 30 travels up wick 32 through capillary action to ovary 20 and stamen 24, which is also formed of conventional wick material such as cotton, and thereafter is dispersed into the air surrounding artificial flower 10 as a floral scent which imitates a real flower. This dispersion is further enhanced with the petals likewise being constructed of suitable fluid-absorbent material whereupon the perfume is transmitted from the ovary 20 to the lower reaches of the petals.

As shown in FIG. 1, ovary 20 and stamen 24 are integrally formed of wick material and include a plastic or metal cover plate 34 with openings 36 therein to provide stability to the wick material while allowing the fragrance of the perfume to be disbursed from the ovary 20. The integral stamen 24 and ovary 20 are attached to wick 32 by means of a pin 38. Such an arrangement allows other floral elements, not shown, to be added to artificial flower 10 if found to be desirable.

FIG. 2 shows a modification of the FIG. 1 arrangement. The flower portion 40 includes a plurality of stamens 24 ending with anthers 18 formed from wick material and mounted on the equivalent of an ovary 20, and connected to wick 32 by a pin 38, wick 32 being located within stem 22. Stem 22 in turn is connected to a schematically shown pressurized container 42, whereby pressure created (by way of example only) by the weight of the top of container 42 against the bottom of container 42 can aid the capillary action in carrying the scented liquid or perfume 30 from container 42 to stamen 24, including anther portion 18. Alternatively, container 42 may be pressurized in a manner similar to that disclosed by U.S. Pat. No. 3,679,133 issued to Sekiguchi et al.

FIG. 3 shows a plurality of artificial flowers 10 mounted on a plurality of stems 44 which merge into a single stem 46 connected to perfume supply container 26. The stems 44 and 46 enclose a wick 48 which extends into container 26 as in FIG. 1. The stamen 24, including filament 16 and anther 18 together with ovary 20, are formed of wick material connected to wick 48 as in FIG. 1 by pin 38.

FIG. 4 shows an arrangement wherein gravity is used to move the perfume from a container 50 held above flower 10 by a suitable bracket 52. The perfume travels through a stem or connecting tube 54 to the anther 18 of stamen 24 because of gravity force, stamen 24 being formed of a wick material as in FIG. 1. If desired, a wick may be provided in tube 54.

As can be seen in each of the disclosed embodiments, the flower scent or perfume is disbursed through the stamen 24 including the filament 16 and anther 18 as well as the ovary portion 20, connected by means of a stem or tube to a perfume container. Additionally, in either embodiment, the perfume may be further transmitted by the ovary 20 to the surrounding petals 12. The perfume may be transferred from the container by capillary action either alone or augmented by pressure, including atmospheric pressure.

While it will be apparent that the preferred embodiment of the invention disclosed is well calculated to fulfill the objects above stated, it will be appreciated that the invention is susceptible to modification, variation and change without departing from the proper scope or fair meaning of the subjoined claims.

I claim:

1. A scented artificial flower comprising:
   a flower cup means formed of petal means;
   at least one integral stamen means including a filament portion and an anther portion extending from and integral with an ovary portion, said integral stamen means and said ovary portion being formed of wick material and located within said flower cup means; and
   a stem means connecting said flower cup means and a perfume container means, said stem means supporting said flower cup means, said integral stamen means and said ovary portion, and a sepal portion, said perfume container means containing scented liquid means; whereby
   said scented liquid means is moved by capillary action through said stem means to said stamen means to be disbursed through said ovary portion, said filament portion and said anther portion to the surrounding atmosphere to thereby simulate a scented flower.

2. A scented artificial flower as in claim 1, wherein:
   said stem means includes a wick means;
   said perfume container means includes a breather cap means;
   said integral stamen means and said ovary portion are connected to said wick means in said stem means by a pin means; and
   said integral stamen means and said ovary portion include a cover plate means having opening means therein to provide stability and support to said integral stamen means and ovary portion.

3. A scented artificial flower as in claim 2, wherein:
   said stem means includes a plurality of branch means, each branch means supporting a flower cup means and an integral stamen means and ovary portion.

4. A scented artificial flower as in claim 1, wherein:
   said integral stamen means and said ovary portion includes a plurality of stamen means each including a filament means and an anther means integral with said ovary portion.

5. A scented artificial flower as in claim 1, wherein:
   said perfume container means is pressurized to aid in the transfer of said scented liquid means from said perfume container means to said stamen means and the disbursement of said scented liquid means from said filament portion, said anther portion and said ovary portion.

6. A scented artificial flower as in claim 1, wherein:
   said perfume container means is located above the level of said flower cup means; and
   said stem means comprises a tube means which connects said perfume container means and said integral stamen means and said ovary portion; whereby
   said scented liquid means is moved from said perfume container means to said integral stamen means and ovary portion with the aid of gravity.

7. A scented artificial flower as in claim 6, wherein:
   said tube means includes a wick means therein connected to said integral stamen means and said ovary portion.

8. A scented artificial flower as in claim 1, wherein:
   said petal means includes a plurality of petals having lower portions engageable with said ovary portion, said petals being formed of wick material, whereby said scented liquid means is further transmitted to said petals.

* * * * *